(12) United States Patent
Lin et al.

(10) Patent No.: US 7,285,254 B2
(45) Date of Patent: Oct. 23, 2007

(54) METHOD AND APPARATUS FOR STERILIZING A LUMEN DEVICE

(75) Inventors: Szu-Min Lin, Laguna Hills, CA (US); Paul Taylor Jacobs, Bicknell, UT (US)

(73) Assignee: Ethicon, Inc., New Brunswick, NJ (US)

( * ) Notice: Subject to any disclaimer, the term of this patent is extended or adjusted under 35 U.S.C. 154(b) by 124 days.

(21) Appl. No.: 11/119,606

(22) Filed: Apr. 29, 2005

(65) Prior Publication Data

US 2005/0191222 A1    Sep. 1, 2005

Related U.S. Application Data

(60) Division of application No. 09/802,326, filed on Mar. 8, 2001, now Pat. No. 6,977,061, which is a continuation-in-part of application No. 09/323,610, filed on Jun. 1, 1999, now Pat. No. 6,528,015, which is a continuation of application No. 08/915,922, filed on Aug. 21, 1997, now Pat. No. 6,066,294, application No. 09/802,326, which is a continuation-in-part of application No. 09/643,336, filed on Aug. 22, 2000, now Pat. No. 6,319,480, which is a continuation of application No. 09/105,491, filed on Jun. 26, 1998, now Pat. No. 6,174,502, which is a division of application No. 08/833,375, filed on Apr. 4, 1997, now Pat. No. 5,961,921.

(51) Int. Cl.
*A61L 2/20* (2006.01)

(52) U.S. Cl. .......................... 422/300; 422/28; 422/33

(58) Field of Classification Search ................ 422/300
See application file for complete search history.

(56) References Cited

U.S. PATENT DOCUMENTS

| | | | |
|---|---|---|---|
| 4,230,663 A | 10/1980 | Forstrom et al. |
| 4,643,876 A | 2/1987 | Jacobs et al. |
| 4,744,951 A | 5/1988 | Cummings et al. |
| 4,756,882 A | 7/1988 | Jacobs et al. |
| 4,797,255 A | 1/1989 | Hatanaka et al. |
| 4,798,292 A | 1/1989 | Hauze |
| 4,863,688 A | 9/1989 | Schmidt et al. |
| 4,937,046 A | 6/1990 | Anderson et al. |
| 4,943,414 A | 7/1990 | Jacobs et al. |
| 4,953,370 A | 9/1990 | Hambright |
| 5,118,471 A | 6/1992 | Anderson et al. |
| 5,122,344 A | 6/1992 | Schmoegner |
| 5,227,132 A | 7/1993 | Andersen et al. |

(Continued)

FOREIGN PATENT DOCUMENTS

WO    WO97/24147 A1    7/1997

*Primary Examiner*—E. Leigh McKane

(57) ABSTRACT

A method and an apparatus for sterilizing a lumen device. A lumen and a container having an interface on a wall of the container are enclosed in a chamber. The lumen is placed across the interface so that one end of the lumen is in the container and the other end is in the chamber. Germicide is introduced into the chamber, and a pressure difference is created between the two ends of the lumen, so that the germicide flows through the lumen. The lumen may alternatively be placed across an interface which separates the chamber into two areas. Germicide is introduced into the chamber, and a pressure difference is created between the two areas of the chamber, causing the germicide to flow through the lumen.

9 Claims, 12 Drawing Sheets

U.S. PATENT DOCUMENTS

| | | |
|---|---|---|
| 5,266,275 A | 11/1993 | Faddis |
| 5,389,336 A | 2/1995 | Childers |
| 5,443,801 A | 8/1995 | Langford |
| 5,445,792 A | 8/1995 | Rickloff et al. |
| 5,492,672 A | 2/1996 | Childers et al. |
| 5,508,009 A | 4/1996 | Rickloff et al. |
| 5,527,508 A | 6/1996 | Childers et al. |
| 5,534,221 A | 7/1996 | Hillebrenner et al. |
| 5,534,222 A | 7/1996 | Kelbrick et al. |
| 5,556,607 A | 9/1996 | Childers et al. |
| 5,633,424 A | 5/1997 | Graves et al. |
| 5,641,464 A | 6/1997 | Briggs, III et al. |
| 5,667,753 A | 9/1997 | Jacobs et al. |
| 5,711,921 A * | 1/1998 | Langford .................... 422/292 |
| 5,846,484 A | 12/1998 | Scarborough et al. |
| 5,961,921 A | 10/1999 | Addy et al. |
| 6,030,579 A | 2/2000 | Addy et al. |
| 6,066,294 A | 5/2000 | Lin et al. |
| 6,162,395 A * | 12/2000 | Kowanko .................... 422/33 |
| 6,174,502 B1 | 1/2001 | Addy et al. |
| 6,224,828 B1 | 5/2001 | Lin et al. |
| 6,319,480 B1 | 11/2001 | Addy et al. |
| 6,365,103 B1 | 4/2002 | Fournier |
| 6,451,255 B1 | 9/2002 | Williams et al. |
| 6,528,015 B1 | 3/2003 | Lin et al. |

* cited by examiner

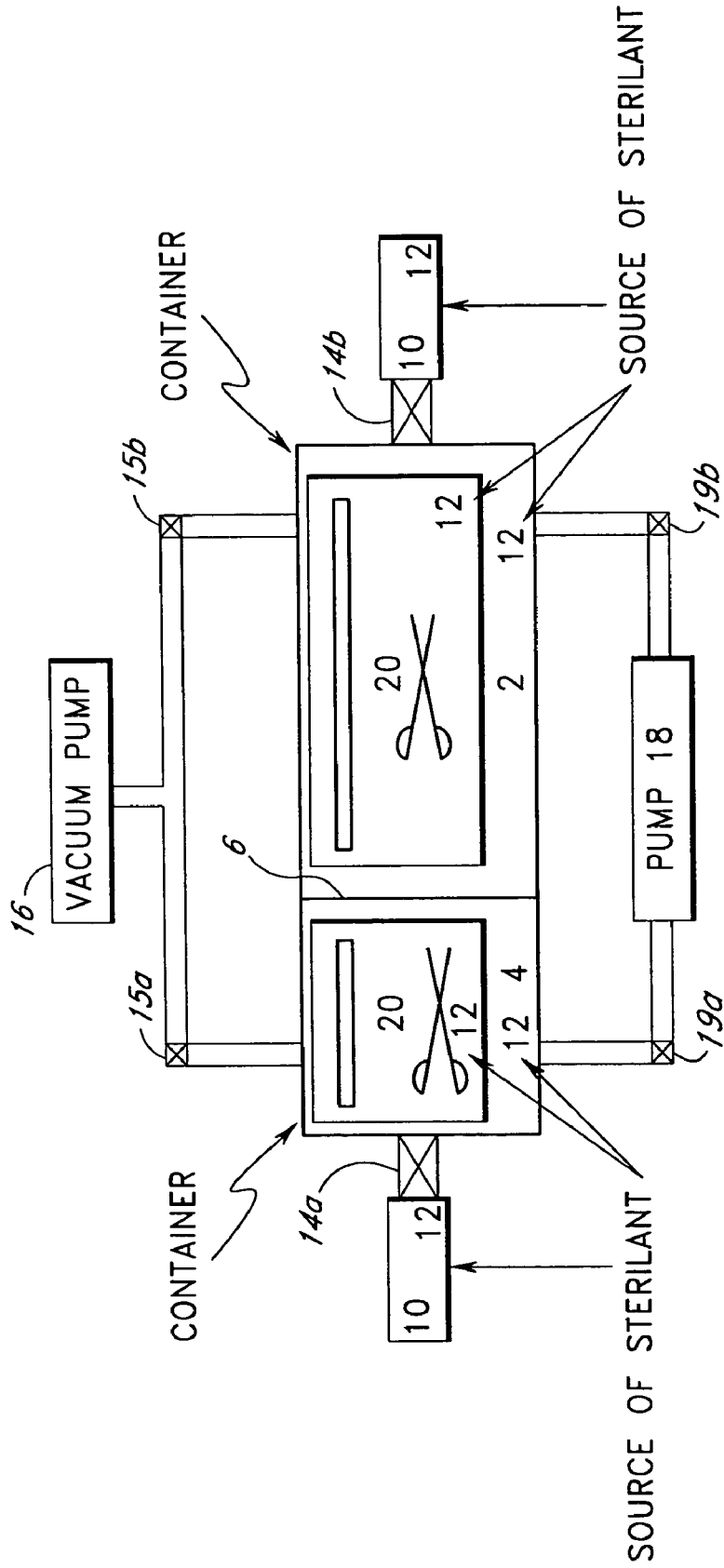

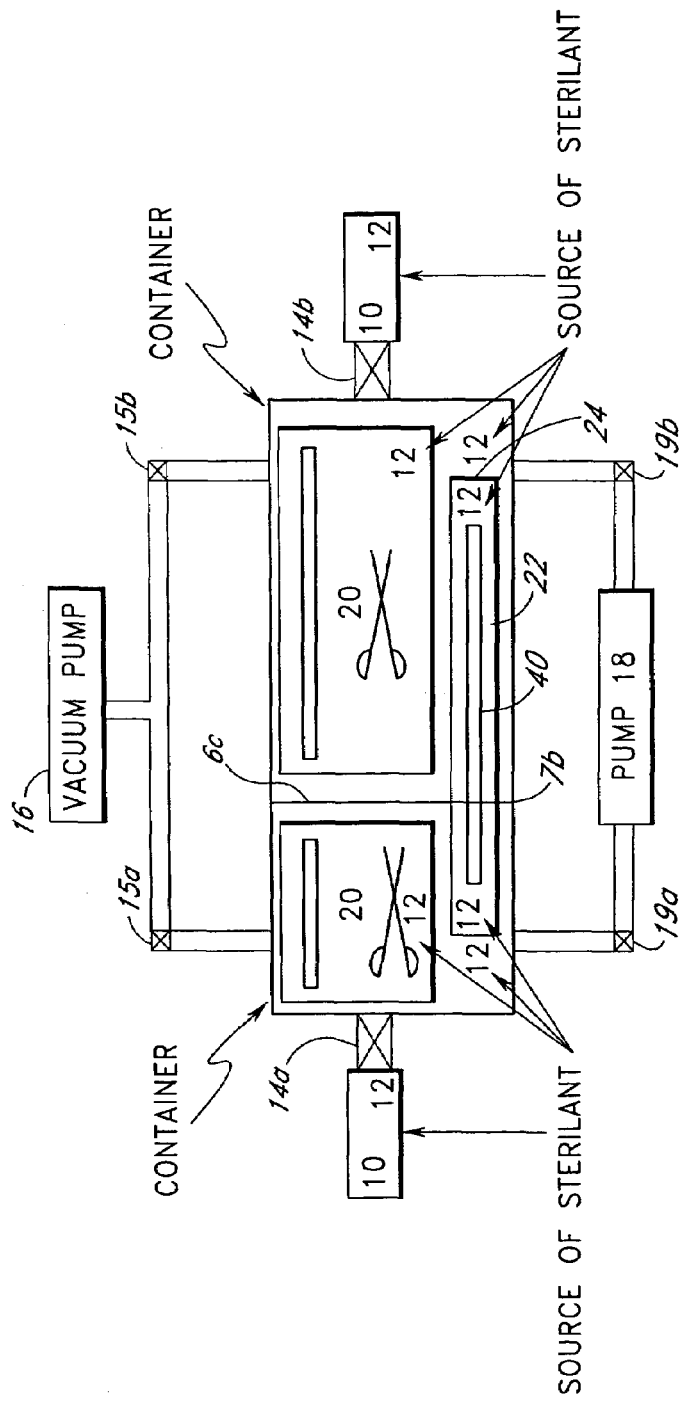
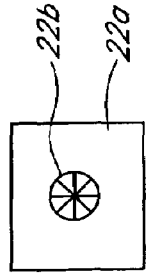
FIG. 6A
FIG. 6B

METHOD AND APPARATUS FOR STERILIZING A LUMEN DEVICE

RELATED APPLICATIONS

This application is a division of application Ser. No. 09/802,326 filed Mar. 8, 2001, now U.S. Pat. No. 6,977,061, which is a continuation-in part of application Ser. No. 09/323,610, filed Jun. 1, 1999, now U.S. Pat. No. 6,528,015, which is a continuation of application Ser. No. 08/915,922, filed Aug. 21, 1997, now U.S. Pat. No. 6,066,294; application Ser. No. 09/323,610 is also a continuation-in-part of application Ser. No. 09/643,336, filed Aug. 22, 2000, now U.S. Pat. No. 6,319,480, which is a continuation of application Ser. No. 09/105,491, filed Jun. 26, 1998, now U.S. Pat. No. 6,174,502, which is a divisional of application Ser. No. 08/833,375, filed Apr. 4, 1997, now U.S. Pat. No. 5,961,921.

BACKGROUND OF THE INVENTION

1. Field of the Invention

The invention relates to systems and methods for chemical sterilization of medical devices with lumens, and more particularly to systems with a container having an interface.

2. Description of the Related Art

Medical instruments have traditionally been sterilized using either heat, such as is provided by steam, or a chemical, in the gas or vapor state. Sterilization using hydrogen peroxide vapor has been shown to have some advantages over other chemical sterilization processes.

The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988 also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles and remove residual hydrogen peroxide. However, effective sterilization of articles having long narrow lumens are very difficult to achieve, since the methods are dependent upon diffusion of the sterilant vapor into close proximity with the article before sterilization can be achieved. Thus, these methods have been found to require high concentration of sterilant, extended exposure time and/or elevated temperatures when used on long, narrow lumens. For example, lumens longer than 27 cm and/or having an internal diameter of less than 0.3 cm have been particularly difficult to sterilize. The sterilization of articles containing long narrow lumens therefore presents a special challenge.

U.S. Pat. No. 4,744,951 to Cummings et al. discloses a two-chambered system which provides hydrogen peroxide in vapor form for use in sterilization processes. The sterilant is initially vaporized in one chamber and then applied to the object to be sanitized in another single sterilizing chamber, thereby producing a concentrated hydrogen peroxide vapor which is relatively more effective. The sterilization processes are designed for furnishing concentrated hydrogen peroxide vapor to interior surfaces of articles having a tortuous or a narrow path. However, the sterilization processes are ineffective at rapidly sterilizing lumened devices, since they depend on the diffusion of the hydrogen peroxide vapor into the lumen to effect sterilization.

U.S. Pat. No. 4,797,255 to Hatanaka et al. discloses a two-chambered sterilization and filling system consisting of a single sterilization chamber adjacent to a germ-free chamber utilized for drying and filling sterilized containers.

U.S. Pat. No. 4,863,688 to Schmidt et al. discloses a sterilization system consisting of a liquid hydrogen peroxide vaporization chamber and an enclosure for sterilization. The enclosure additionally may hold containers wherein the hydrogen peroxide sterilant vapor does not contact the interior of the containers. This system is designed for controlling the exposure to the hydrogen peroxide vapor. The system is not designed for sterilizing a lumen device.

U.S. Pat. No. 4,952,370 to Cummings et al. discloses a sterilization process wherein aqueous hydrogen peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized.

U.S. Pat. Nos. 4,937,046, 5,118,471 and 5,227,132 to Anderson et al. each disclose a sterilization system which uses ethylene oxide gas for sanitation purposes. The gas is initially in a small first enclosure and thereafter slowly permeates into a second enclosure where the objects to be sterilized are located. A medium is then introduced into the second enclosure to flush out the sterilizing gas into a third enclosure containing the second enclosure. An exhaust system then exhausts the sterilant gas and air from the third enclosure. These systems also have the disadvantage of relying on the diffusion of the sterilant vapor to effect sterilization and hence are not suitable for rapidly sterilizing lumened devices.

U.S. Pat. No. 5,122,344 to Schmoegner discloses a chemical sterilizer system for sterilizing items by vaporizing a liquid chemical sterilant in a sterilizing chamber. Pre-evacuation of the sterilizer chamber enhances the sterilizing activity. Sterilant is injected into the sterilizer chamber from a second prefilled shot chamber. This system also relies upon diffusion of sterilant vapor to effect sterilization and is also not suitable for rapidly sterilizing lumened devices.

U.S. Pat. No. 5,266,275 to Faddis discloses a sterilization system for disinfecting instruments. The sterilization system contains a primary sterilization chamber and a secondary safety chamber. The secondary safety chamber provides for sensing and venting to a destruction chamber any sterilization agent that is released from the primary sterilization chamber. This system, as in other systems, also relies upon diffusion of sterilant vapor to effect sterilization and is also not suitable for rapidly sterilizing lumened devices.

In U.S. Pat. Nos. 5,492,672 and 5,556,607 to Childers et al, there is disclosed a process and apparatus respectively for sterilizing narrow lumens. This process and apparatus uses a multicomponent sterilant vapor and requires successive alternating periods of flow of sterilant vapor and discontinuance of such flow. A complex apparatus is used to accomplish the method. Additionally, the process and apparatus of '672 and '607 require maintaining the pressure in the sterilization chamber at a predetermined subatmospheric pressure.

In U.S. Pat. No. 5,527,508 to Childers et al., a method of enhancing the penetration of low vapor pressure chemical vapor sterilants into the apertures and openings of complex objects is disclosed. The method repeatedly introduces air or an inert gas into the closed sterilization chamber in an amount effective to raise the pressure to a subatmospheric pressure to drive the diffused sterilant vapor further into the article to achieve sterilization. The '508, '672 and '607 Childers inventions are similar in that all three require repeated pulsations of sterilant vapor flow and maintenance of the sterilization chamber pressure at a predetermined subatmospheric pressure.

In U.S. Pat. No. 5,534,221 to Hillebrenner et al., a device and method for sterilizing and storing an endoscope or other lumened medical device is disclosed. The device includes a sealable cassette in which the endoscope or other medical device is placed. The cassette has an input port for receiving a sterilizing agent through a connector, an output port for expelling the sterilizing agent when a vacuum is applied thereto through a connector, and check valves in the input and output ports to open the ports when the connectors are coupled to the ports and to seal the ports when the connectors are removed from the ports such that after the endoscope has been sterilized, it remains sterilized within the cassette until the cassette is opened. The method of the '221 invention involves placing the medical device inside the cassette and coupling the device to either the input or output port of the cassette. The cassette is then placed in an outer oven-like container or warming chamber where the temperature is properly maintained. Connections are made to open the input and output ports on the cassette such that the sterilizing agent may be introduced through a first port to bathe the outside of the medical instrument or other object, such as an endoscope while one end of the hollow object, such as the endoscope, is coupled to the output port where a vacuum is supplied external to the cassette to pull the sterilization agent into the cassette and through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. Thus, the '221 invention is concerned with providing a means whereby a sterilized medical device can be retained within a cassette in which it was sterilized until ready for use, thus avoiding any contamination by exposure to the atmosphere or handling before use. Additionally, in some cases of the '221 invention, wherein the lumen of the device to be sterilized is connected to the output port, particularly wherein the devices have long, narrow lumens, the time to expel the sterilizing agent through the lumen and out of the cassette may be undesirably long. Also, in cases wherein the lumen device is very flexible, lumen collapse may occur, either slowing or preventing vapor exit or causing lumen damage.

U.S. Pat. Nos. 5,445,792 and 5,508,009 to Rickloff et al. each disclose a sterilization system essentially equivalent to the system disclosed in Hillebrenner '221.

U.S. Pat. No. 5,443,801 to Langford teaches a transportable cleaning/sterilizing apparatus and a method for inside-outside sterilization of medical/dental instruments. The apparatus avoids the use of heat, pressure, severe agitation, or corrosive chemicals which might damage delicate equipment. This invention uses ozone gas or solution as sterilant. It does not involve the use of sterilant vapor or vaporizing a sterilant solution into vapor, and is not suitable for operations under vacuum because flexible bags or containers are used.

In consideration of the foregoing, no simple, safe, effective method of sterilizing smaller lumens exists in the prior art. Thus, there remains a need for a simple and effective method of vapor sterilization of articles with both long, narrow lumens as well as shorter, wider lumens. Furthermore, there also remains a need for a simple and effective sterilization system with independently operable chambers.

SUMMARY OF THE INVENTION

One aspect of the invention involves a method for enhancing the sterilization of a lumen, where the lumen has at least a first end and a second end. The method includes enclosing the lumen and a container in a chamber, where the container has at least one interface on a wall of the container, and where the container does not contain germicide. The lumen is placed across the interface such that one end of the lumen is in the container and the other end of the lumen is in the chamber. The method also includes introducing a germicide into the chamber, creating a higher pressure in the chamber than in the container, and flowing the germicide from the chamber into the container through the lumen.

Advantageously, the chamber is evacuated before the germicide is introduced into the chamber. Preferably, the chamber is evacuated after the germicide flows from the chamber into the container through the lumen. In an embodiment, the chamber is vented after the germicide flows from the chamber into the container through the lumen. Preferably, the germicide includes hydrogen peroxide. Advantageously, the interface includes at least one opening. In an embodiment, the opening includes a material which is permeable to the germicide, whereby the contact area between the interface and the lumen is contacted with the germicide. The method may also include adjusting the opening. Preferably, the container is evacuated through a communication port in the container, where the communication port is different from the opening.

Another aspect of the invention involves a system for sterilizing a lumen, where the lumen has at least a first end and a second end. The system includes a container with at least one interface on a wall of the container, where the container does not contain germicide. The system also includes a chamber which contains the container. The lumen is placed across the interface such that the first end of the lumen is in the container and the second end of the lumen is in the chamber. The system also includes at least one pump to evacuate the chamber and the container and a source of germicide.

The source of germicide may be in the chamber or in an enclosure in fluid communication with the chamber. Preferably the source of germicide includes hydrogen peroxide. Advantageously, the interface has at least one opening. In an embodiment, the opening includes a material which is permeable to germicide generated from the source of germicide, where the material is located at least in the contact area between the interface and the lumen. Preferably, the container also includes a communication port in fluid communication with the pump, where the communication port is different from the opening. In an embodiment, the opening is adjustable.

Another aspect of the invention involves a system for sterilizing a lumen device. The system includes a chamber having at least one interface, where the interface separates the chamber into a first area and a second area. The system also includes a source of germicide and a container inside the chamber, where at least a portion of the container is located in the first area of the chamber and a least a portion of the container is located in the second area of the chamber. The container includes at least one interface, where the interface separates the container into at least a first compartment and a second compartment. The container also includes at least one communication port, where the communication port provides fluid communication between the container and the chamber. The container includes at least one lumen device extending across the interface in the container, whereby the first compartment is in fluid communication with the second compartment through the lumen device.

Preferably, the interface includes at least one opening. Advantageously, the opening is adjustable. In an embodiment, the opening includes a material which is permeable to germicide generated from the source of germicide, where the material is located at least in the contact area between the interface and the lumen. Preferably, the system also includes at least one vacuum pump to evacuate the chamber and/or the container. Advantageously, the source of germicide includes hydrogen peroxide. In an embodiment, the communication port includes a gas or vapor permeable membrane. Preferably, the gas or vapor permeable membrane is impermeable to microorganisms. In an embodiment, at least one communication port provides fluid communication between the first compartment and the chamber and at least one communication port provides fluid communication between the second compartment and the chamber.

Yet another aspect of the invention involves a method for sterilizing a lumen device The method includes enclosing a container in a chamber, where the container includes an interface, where the interface separates the container into a first compartment and a second compartment. The container also includes at least one lumen device extending across the interface, whereby said the first compartment is in fluid communication with the second compartment through the lumen device. The container also includes at least one communication port in the container, where the communication port provides fluid communication between the container and the chamber. The method includes providing a germicide in at least one of the chamber, the container, and an enclosure in fluid communication with the chamber. A pressure difference is created between the chamber and the container, creating a pressure difference between the first compartment and the second compartment. The germicide flows between the chamber and the container through the communication port in the container and between the first compartment and the second compartment through the lumen device.

Advantageously, the germicide includes hydrogen peroxide. Preferably, the method also includes removing the container from the chamber. In an embodiment, the sterility of the lumen device is maintained in the container. Preferably, the interface includes at least one opening. Advantageously, the opening includes a material which is permeable to the germicide, whereby the contact area between the interface and the lumen is contacted with the germicide. The method may also include adjusting the opening.

Another aspect of the invention involves a system for sterilizing a lumen device in a chamber, where the system includes a vacuum chamber, an interface, where the interface separates the vacuum chamber into a first compartment and a second compartment, and at least one lumen device extending across the interface, whereby the first compartment is in fluid communication with the second compartment through the lumen device. The system also includes a source of germicide and at least one vacuum pump.

Advantageously, the interface includes at least one opening. Preferably, the opening is adjustable. In an embodiment, the opening includes a material which is permeable to germicide generated from the source of germicide, where the material is located at least in the contact area between the interface and the lumen. Advantageously, a germicide vapor or gas is generated from the source of germicide. Preferably, the source of germicide includes hydrogen peroxide.

Another aspect of the invention involves a method for sterilizing a lumen device in a vacuum chamber. The method includes separating the vacuum chamber into a first compartment and a second compartment with an interface, where at least one lumen device extends across the interface, whereby the first compartment is in fluid communication with the second compartment through the lumen device. The method also includes evacuating the vacuum chamber, thereby decreasing the pressure in the first compartment and the second compartment. The method also includes introducing germicide into at least one of the first compartment and the second compartment, where introducing occurs after evacuating, and creating a pressure difference between the first compartment and the second compartment, thereby flowing germicide between the first compartment and the second compartment through the lumen device.

Advantageously, the germicide includes hydrogen peroxide. Preferably, the interface includes at least one opening. In an embodiment, the opening includes a material which is permeable to the germicide, whereby the contact area between said interface and said lumen is contacted with germicide. The method may also include adjusting the opening. Advantageously, the method also includes increasing the pressure in the first compartment and the second compartment, where the pressure is increased after the germicide is introduced and after a pressure difference is created between the first compartment and the second compartment.

BRIEF DESCRIPTION OF THE DRAWINGS

FIG. 5 is a schematic diagram of an embodiment of the apparatus of the present invention showing two chambers containing containers;

FIG. 6A is a schematic diagram of an embodiment of the apparatus of the present invention showing two chambers containing containers and being connected through a lumen;

FIG. 6B is a cross sectional view of the system of FIG. 6A;

DETAILED DESCRIPTION OF THE PREFERRED EMBODIMENT

Figure 1A:
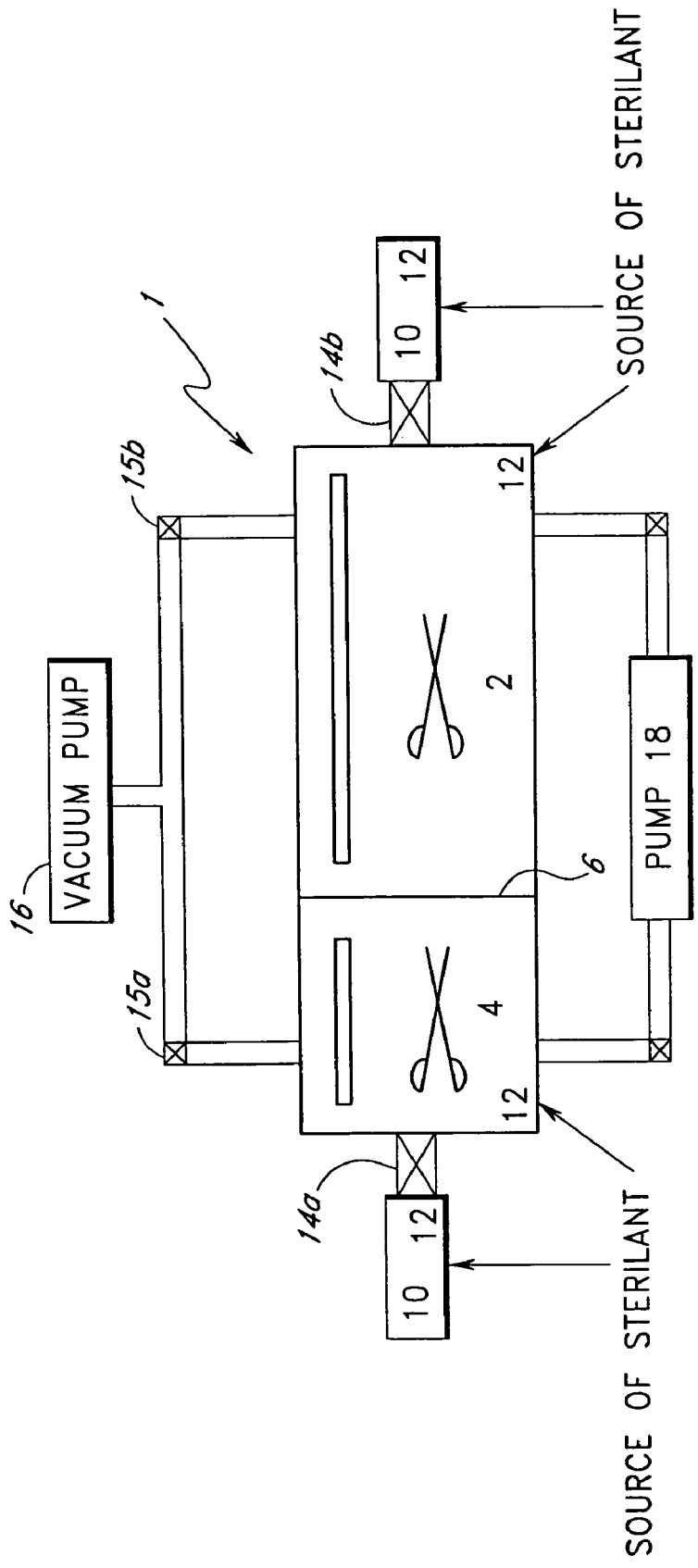
FIG. 1A is a schematic diagram of an embodiment of the apparatus of the present invention showing two chambers separated with a sealable interface.

The multi-compartment sterilization apparatus of the present invention is suitable for the sterilization of both non-lumen and lumen devices.

According to one aspect of the present invention, the multi-compartment sterilization apparatus comprises at least two chambers separated by a sealable and removable interface. Each of the chambers can be operated independently and serve as a sterilization chamber. In a sterilization process using the apparatus of the present invention, the interface can be adjusted for different situations. For example, if the device to be sterilized is too big to fit into either one of the two chambers, the interface can be removed so that more space will be available to accommodate the device. If the device is not so big, it can be sterilized in one of the two chambers while other devices can be prepared for sterilization in the other chamber.

According to another aspect of the present invention, the multi-compartment sterilization apparatus comprises a sterilization system with a multi-chambered compartment having at least a first rigid chamber and a second rigid chamber, an openable and closeable interface between the first and second chamber, a flow path between the first and second chamber, and a source of sterilant adapted to provide the sterilant in the first and/or second chamber. The flow path can be a lumen of the device to be sterilized, so that sterilant can flow directly through the lumen to sterilize the interior of the lumen device. Different sterilization methods and technologies can be used in corporation with the sterilization system of the present invention. Several embodiments of those methods are described below:

Method to Deliver a Predetermined Amount of Liquid Sterilant

Conventional sterilants can be used in the present invention. Numerous sterilants are available in the art, such as formaldehyde, ethylene oxide, hydrogen peroxide solution and hydrogen peroxide vapor. Although any of those sterilants can be used in the sterilization apparatus of the present invention, the use of hydrogen peroxide solution and hydrogen peroxide vapor has been shown to have some advantages over other chemical sterilization processes. Therefore, it is preferred to use hydrogen peroxide solution and hydrogen peroxide vapor as sterilant in the present invention. In a sterilization process using hydrogen peroxide solution as sterilant, the sterilant can be applied in several different ways. For example, a hydrogen peroxide solution can be first vaporized under vacuum and/or heat in a vacuum chamber, and the device to be sterilized is then exposed to the hydrogen peroxide vapor. Accordingly, in one embodiment of the present invention, an important parameter of the process needed to achieve satisfactory sterilization is the amount of liquid hydrogen peroxide entering into the chamber to be vaporized. Thus, it is important that the liquid hydrogen peroxide be delivered to the chamber in measured quantities.

A sterilization apparatus able to deliver a predetermined amount of liquid sterilant can be incorporated into the sterilization system of the present invention. Thus, the sterilization chamber may have a bottom wall with at least one well which defines a known volume. The well is positioned so that when a liquid sterilant is introduced onto the bottom surface, a known volume of the liquid sterilant fills the well and when the liquid sterilant is drained from the surface, the known volume of liquid sterilant remains in the well so that a subsequent sterilization process can be performed on the device positioned on the bottom surface with the known volume of liquid sterilant positioned within the bottom surface. The apparatus may also include a heat source and/or a vacuum source for vaporizing the liquid sterilant in the well, and can optionally include a source of plasma. The bottom surface preferably has at least one perforation for draining the liquid sterilant from the bottom surface. The well formed in the bottom surface can be curved, flat or angled. Thus, the well can be an inwardly extending hemispherical projection. The well can also be formed in the bottom surface as an inwardly extending rectangular projection having rounded ends. The well formed in the bottom surface can also be a rectangular box having side walls, defining an opening. Where perforations are provided, they can be disposed adjacent the well, and can be roughly spherical in shape. The upwardly extending projection can include a perforation thereon, which can be on top of the projection or on a side of the projection. The bottom surface can be a sloped surface, a convex or concave surface or a V-shaped surface. The bottom surface can be of a variety of materials including stainless steels, aluminum, aluminum alloys, liquid crystal polymers, polyesters, polyolefin polymers or fluorinated polyolefins. If the bottom surface is comprised of a composite material, the composite material can include a filler of high thermal conductivity. Examples of composite materials include a metal-filled polymer, a ceramic-filled polymer and a glass-filled polymer. Those materials are also suitable for the side walls and doors of the sterilization chamber.

Method Based on Diffusion Restricted Environments

A method of hydrogen peroxide vapor sterilization of diffusion-restricted environments can also be used in corporation with the present invention. In this embodiment of the present invention, the devices (lumen or non-lumen) to be sterilized are pretreated with a hydrogen peroxide solution, and then exposed to pressures less than the vapor pressure of sterilant. The inside of lumens is sterilized by taking advantage of the diffusion-restricted environments within the lumens.

As used herein, a "diffusion-restricted" area refers to any one or more of the following properties: (1) the ability of the area of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

In this embodiment of the present invention, a method for sterilizing an interior of a device with a diffusion restricted area, such as a device having a lumen, is used in corporation with the sterilization system. The method includes the steps of contacting the interior of the device with a liquid solution comprising hydrogen peroxide, and exposing the device to negative pressure for a time period sufficient to effect complete sterilization. In one embodiment, the liquid solution is peracetic acid. If the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The solution is preferably at a concentration of less than 25% by weight. The contacting step can be performed by delivery via a method such as injection, static soak, liquid flow-through or aerosol spray. In a preferred embodiment, the diffusion-restricted area is a lumen at least 27 cm in length and having an internal diameter of no more than 3 mm, more preferably having an internal diameter of no more than 1 mm. The exposing step is preferably performed for 60 minutes or less, and is preferably performed at a pressure less than the vapor pressure of hydrogen peroxide. Thus, the preferred pressure range under conditions of the present invention is between 0 and 100 torr. In one particularly preferred embodiment, the pressure is approximately 10 torr and the exposing step is conducted at a temperature of approximately 23° C. to approximately 28° C. The exposing step can include the step of heating the article, such as by heating the chamber in which the exposing step occurs. The chamber can be heated to about 30° C. to about 45° C. Alternatively, the solution can be heated, such as to a temperature of about 30° C. to about 45° C. Optionally, the step of exposing the device to a plasma can be conducted during the step of exposing the device to negative pressure. In one embodiment employing exposure to plasma, the method is performed within a first chamber and the plasma is generated in a second, separate chamber. This embodiment further comprises the step of flowing the plasma into the first chamber. Advantageously, the contacting and/or exposing steps of the method can be repeated one or more times.

Sterilization Methods in Non-diffusion Restricted Environments

The present invention can also be used to sterilize devices with lumens without relying on a diffusion-restricted environment.

It has been discovered by the inventors that similar sterilization results to those created in diffusion-restricted environments can be created through controlling the evacuation rate of the chamber in which articles to be sterilized are placed. Thus, in one embodiment of the present invention, a method for sterilizing a device can be used in corporation with the sterilization system of the present invention. The method comprises the steps of contacting the device with liquid sterilant outside or inside a sterilization chamber at a first pressure; placing the device in the chamber before or after the contacting step; and decreasing the pressure of the chamber to a second pressure below the vapor pressure of the liquid sterilant in which at least a portion of the decrease in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry, i.e. when the chamber has neither articles to be sterilized nor a visible quantity of liquid within it. According to one aspect of this preferred embodiment, at least the decrease in pressure below about two times the vapor pressure of the liquid sterilant occurs at a pumpdown rate of less than 0.8 liters per second. According to another aspect of this embodiment, the decrease in pressure below about four times the vapor pressure of the liquid sterilant occurs at a pumpdown rate of less than 0.8 liters per second. Preferably, the pumpdown rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. In another aspect, the device is a medical instrument having a lumen.

The present invention can also use a method for sterilizing a device comprising the steps of (a) contacting the device with liquid sterilant outside or inside a sterilization chamber at a first pressure; (b) placing the device in the chamber before or after the contacting step; (c) pumping down the chamber to a second pressure which is lower than the first pressure at a first rate; and (d) pumping down the chamber to a third pressure which is lower than the second pressure, wherein at least a portion of the pumping down to the third pressure is at a second rate which is slower than the first rate. The pumpdown rate either above and/or below the second pressure can be constant or variable. In certain embodiments, the pumpdown rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pumpdown rate in step (d) is 0.8 liters/sec or less; more advantageously 0.6 liters/sec or less; even more advantageously 0.4 liters/sec or less; and most advantageously 0.2 liters/sec or less, calculated based on the time required to evaluate the chamber from atmospheric pressure to 20 torr under empty and dry conditions. Preferably, the liquid sterilant is hydrogen peroxide. In another aspect of this embodiment, the device is a medical instrument having a lumen. Preferably, the pumping down of step (c) reduces the pressure to less than about three times, more preferably to less than about two times, the vapor pressure of the liquid sterilant.

Another suitable method includes contacting the article with liquid sterilant either inside or outside of the sterilization chamber, placing the device in the chamber either before or after the contacting step, and reducing the pressure of the chamber while regulating the pumpdown rate so as to control the evaporation rate of sterilant in said chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated hereinbelow, indirect contacting involves introducing sterilant into the chamber without directly contacting the article to be sterilized.

In another embodiment, a two step pump down sterilization process can be used in connection with the sterilization system of the present invention. The method comprises the steps of: contacting a device with liquid sterilant outside or inside a sterilization chamber; placing the device in the chamber before or after the contacting step; bringing the pressure of the chamber to a first pressure range at which liquid sterilant is vaporized from the non-diffusion restricted area to sterilize the non-diffusion restricted area; bringing the pressure of the chamber to a second pressure range at which the liquid sterilant is vaporized from the diffusion restricted area to sterilize the diffusion restricted area, wherein the minimum pressure in the second pressure range is lower than the maximum pressure in the first pressure range.

Preferably, the first pressure range is 20 to 760 torr; more preferably, the first pressure range is 20 to 80 torr; most preferably, the first pressure range is 40-50 torr. Advantageously, the second pressure range is 1-30 torr; more advantageously, the second pressure range is 5-10 torr. In one aspect of this preferred embodiment, the device includes a diffusion-restricted environment. Preferably, the device is a medical instrument with a lumen having an interior and an exterior surface. Advantageously, the sterilant is hydrogen peroxide. According to another aspect of this preferred embodiment, the chamber is at a set temperature and wherein the first pressure is greater than the vapor pressure of the sterilant at the set temperature. Preferably, the pressure of the chamber is maintained constant at the first pressure for a time period sufficient to sterilize the non-diffusion restricted area. Advantageously, the pressure of the chamber is maintained constant at the second pressure for a time period sufficient to sterilize the diffusion restricted area. The pressure of the chamber may be permitted to increase after reaching the first or second pressure range as a result of vaporization of the sterilant within said chamber. Alternatively, the pressure of the chamber is permitted to decrease after reaching the first or second pressure through pumping of said chamber at a rate slower than used to decrease the pressure between said first and second pressure ranges. Preferably, the contacting step is with liquid or condensed vapor. The method can also include the steps of bringing the pressure to a third pressure lower then the second pressure to remove residual sterilant and/or exposing the device to plasma to remove residual sterilant or enhance sterilization efficacy.

Method Involving Direct Flow Through a Lumen of Devices to be Sterilized

According to the present invention, a sterilization apparatus is provided which can more efficiently sterilize devices with long narrow lumens by flowing a sterilant, either in liquid phase or in vapor phase, directly through the lumens of lumen devices to be sterilized.

The flow of a sterilant (solution or vapor) through a lumen of a medical device is realized by a pressure drop between two ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

It is clear from the above discussion that the two ends of the lumen need to be exposed to a pressure differential. This is achieved in the present invention by placing a sealable interface between the two chambers. An opening is provided in the interface and the lumen device to be sterilized is placed through the opening in such a way that the lumen serves as a flow path between the two chambers.

The opening can be constructed in several ways. One way to achieve this is with a camera shutter approach employing an iris diaphragm, such as a precision iris diaphragm from Edmund Scientific. An optional spring can be used to secure the closure of the shutter. Another way to achieve an acceptable opening is to employ two plates, wherein the area between the two plates has a compressible material, such as a rubber material. The lumen device can be placed between the two plates and the two plates moved together to form a gas and vapor impermeable seal around the lumen device. Optionally, a porous material like a sponge or air permeable material may be utilized for the compressible material. In this case some sterilant can flow between the compressible material and the lumen device. However, most the sterilant flows through the lumen device. Yet another acceptable interface is a hole or horizontal opening for one or more lumen devices, said hole or opening being a gas or liquid inflatable so that by inflating the inflatable material on the hole or opening the lumen devices are held and sealed. Still another option is to place a compressible material on top of an inflatable material so as to facilitate the sealing around the lumen device.

The closing and opening movement of the opening such as the plate and the iris diaphragm can be controlled mechanically or electronically with any conventional mechanism.

It is sealed to a different degree between the opening and the lumen device depending on the desired purpose. For example, the opening can form a gas-tight seal around the lumen device so that nothing can flow outside of the lumen device through the opening; or form a loose-fitting seal around the lumen device allowing sterilant to flow outside of the lumen device through the opening so that the exterior of the lumen device adjacent the opening can be sterilized; or form a tight-fitting with a porous material, such as a gas and/or liquid permeable membrane around the lumen device so that gas and sterilant can pass and, in the meantime, the porous material helps to hold the lumen device. The interface can be made openable, closeable, and removable. A flow path between different chambers can be also provided outside the sterilization system.

In order to promote sterilization efficiency, all the sterilization apparatus of the present invention can be further equipped with a heater, vacuum, and/or a plasma.

The present invention is further described in connection with the drawings below. In the following FIGURES like numbers refer to like parts throughout. Referring to FIG. 1A, the sterilization apparatus comprises a first chamber 2 and a second chamber 4. The two chambers are separated by a sealable and removable interface 6 so that the two chambers can be operated independently, i.e. different items can be sterilized simultaneously in the two chambers, or one chamber is operated for sterilization while the other is not in operation. An enclosure 10 for receiving a steriliant source 12 is connected to each of chambers 4 and 2 through a valve 14a and a valve 14b, respectively. Two enclosures 10 are shown in FIG. 1A. However, these two enclosures 10 can be combined into one. Enclosure 10 can be made of materials similar to those of the walls of chambers 2 and 4. The steriliant source 12 can be located in one or more locations of enclosure 10, chamber 2, and/or chamber 4. There are several way to control the amount of steriliant entering chamber 2 or 4 if such control is desired. For example, valves 14a and 14b can be a metering valve and the amount of steriliant flowing from enclosure 10 to chambers 2 and 4 is measured and controlled by valve 14a or 14b; or enclosure 10 is equipped with a volume reading so that the volume of the steriliant in enclosure 10 can be read; or steriliant containing wells (not shown) can be provided in the chambers to control the amount of liquid steriliant. The steriliant source 12 can be also located in chamber 2 and/or chamber 4.

Chambers 2 and 4 are equipped with a vacuum pump 16 for generating vacuum within these chambers during the sterilization process. Valve 15a and valve 15b are provided connecting vacuum pump 16 to chamber 4 and 2, respectively. They are controlled independently. Chambers 2 and 4 can also be equipped with a pump 18 to circulate steriliant between the two chambers. Chambers 2 and 4 can be of any desired shape, but a regular shape such as cylindrical or rectangular will make it easier to accommodate the interface 6.

Figure 1B:
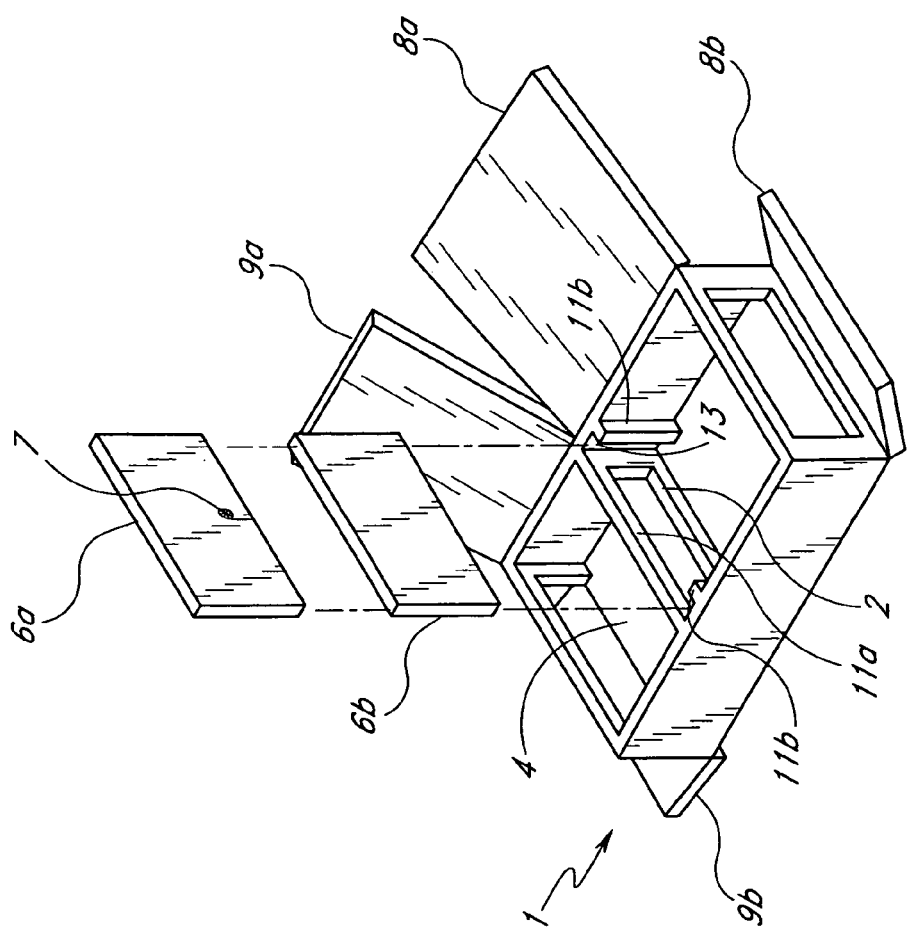
FIG. 1B is a schematic diagram of an embodiment of the apparatus of the present invention showing the interface, doors and two chambers.

FIG. 1B shows more details of chambers 2 and 4 with interface and doors. As shown in this FIGURE, chambers 2 and 4 can be equipped with doors 8a, 8b, 9a, and 9b, respectively. One chamber does not necessarily have more than one door. There are a frame 11a and a guiding piece 11b between the two chambers. Interface 6a or 6b is secured between the two chambers through frame 11a and guiding piece 11b by sliding the interface into gap 13 defined by frame 11a and guiding piece 11b. If necessary, interface 6a or 6b can be further secured to frame 11a by any conventional means, such as screw or clamp. A sealing O-ring (not shown) can be provided around the frame 11a to generate a good sealing between the two chambers. The interface 6a has an opening 7 adapted to receive a lumen device. Opening 7 may have different shape and size to accommodate different types of lumen devices. Under different situation, different interface can be chosen. The opening 7 is controllable. In one embodiment the opening has a shutter structure which is electrically controlled. By changing the dimension of the opening, different degree of seal between the opening and the lumen device held by the opening can be achieved.

Figure 2:
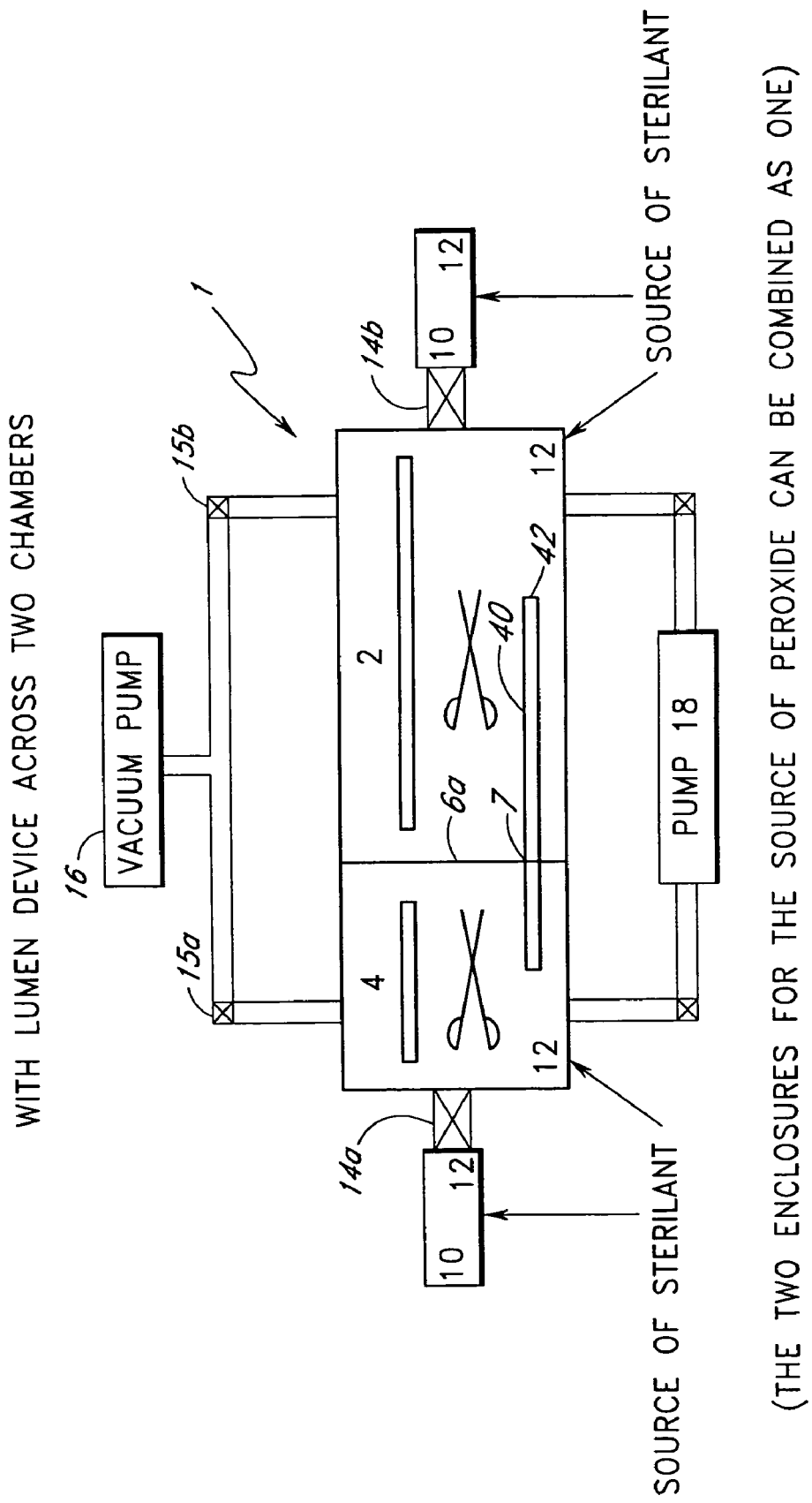
FIG. 2 is a schematic diagram of an embodiment of the apparatus of the present invention showing two chambers separated by an interface and in fluid communication through a lumen device.

FIG. 2 shows a sterilization apparatus able to generate a steriliant flow through a lumen to be sterilized. As shown in FIG. 2, the apparatus comprises a first chamber 2 and a second chamber 4. The two chambers are separated by an openable and closeable interface 6a. Interface 6a has an opening 7. A lumen device 40 with a lumen 42 is placed through the opening 7 in such a way that one end of the lumen 42 is in chamber 2 and the other end in chamber 4. At least during a part of a sterilization process for sterilizing the interior of the lumen 42, the opening 7 is gas-tight sealed around the lumen device 40 so that steriliant fluid flows through the lumen 42 under a pressure drop between the two chambers 2 and 4. Although a liquid steriliant can be used in the apparatus, steriliant vapor is preferred. The steriliant vapor can be generated with any appropriate method known to the art or with the method described in the copending application referenced previously. Generally speaking, the usual way to generate vapors in a sterilization system is the use of heating and/or vacuum. In the present invention, both heating and vacuum can be employed to generate steriliant vapor.

In order to generate a flow of steriliant fluid through the lumen 42, pressure differential has to be exist between the two ends of the lumen 42. One way of generating such a pressure gradient is to pressurize one end of the lumen 42. But it is more desirable to apply vacuum to one end of the lumen 42 with vacuum pump 16, especially when steriliant vapor is used. The two chambers can be operated either under vacuum or under pressure up to about 4 atmospheres. The temperature of the two chambers can be controlled independently through a conventional heating device (not shown). The operation temperature of the chambers are adjusted so as not to damage the device to sterilized. It is usually below 80° C., more preferably 20-55° C.

Vacuum pump 16 is used to generate vacuum in either chamber 2 or chamber 4 through valve 15b and 15a. Pump 18 is used to circulate steriliant between chamber 2 and chamber 4. If necessary, vacuum pump 16 and air pump 18 can be operated either simultaneously or sequentially.

In addition to lumen device 40, a plurality of devices can be sterilized in both chamber 2 and 4. In this embodiment, the devices to be sterilized can be pretreated or not pretreated with liquid steriliant. Because steriliant is circulated through the lumen 42, the interior of the lumen device 40 is mainly sterilized by the steriliant flow therethrough. This direct circulation of steriliant provides an efficient sterilization of the interior of the lumen 42, especially, when hydrogen peroxide vapor is circulated through the lumen 42. Doors can be provided for the two chambers at any convenient locations, for example, as shown in FIG. 1B. Steriliant can be provided from enclosure 10, or directly from the source of steriliant 12. The steriliant source 12 can be in the form injection, static soak, liquid flowthrough, or aerosol spray. Liquid steriliant may also be placed on the wells (not shown) on the bottom surface of the chambers and is vaporized during the sterilization by applying vacuum and/or heating.

All the features and functions of the apparatus shown in FIG. 1A and described previously are applicable to the apparatus shown in FIG. 2.

Figure 3:
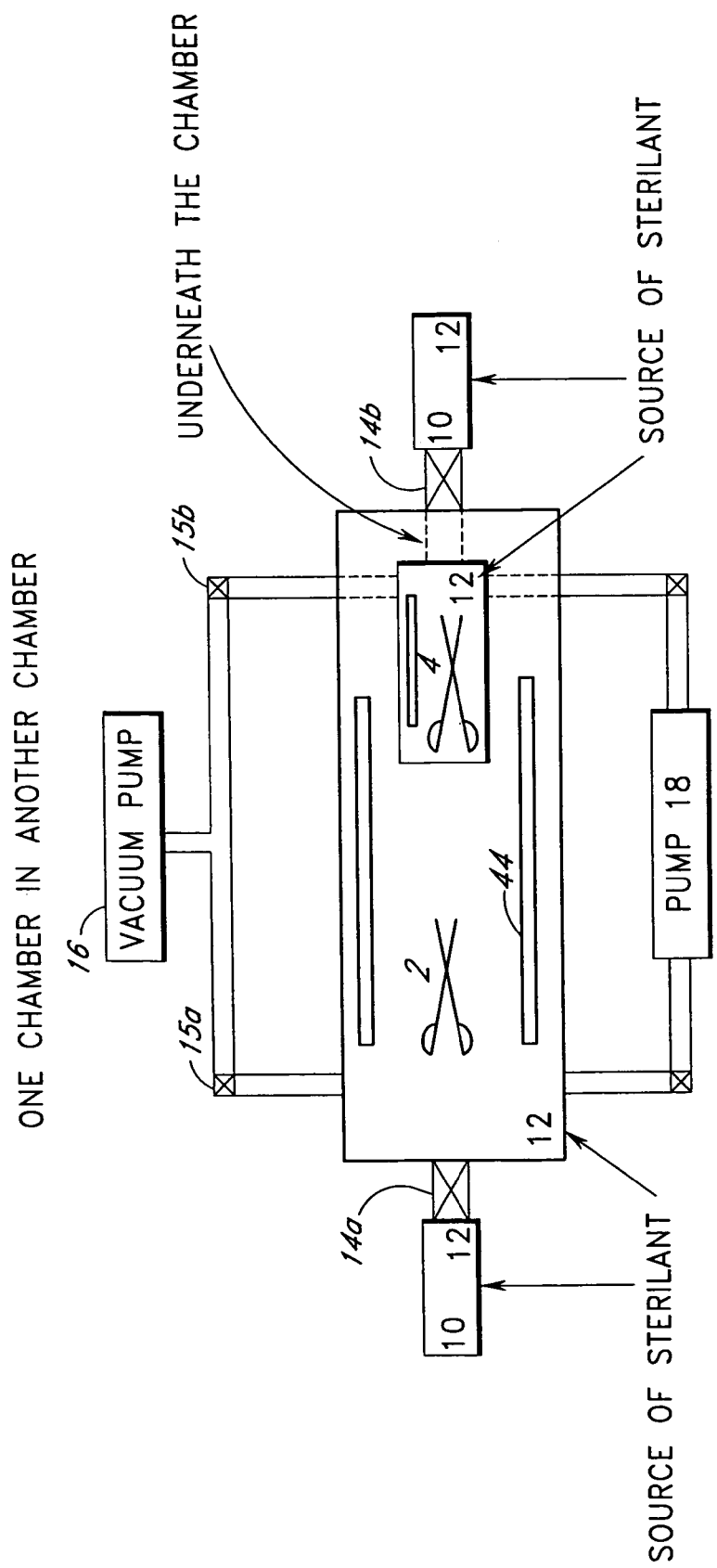
FIG. 3 is a schematic diagram of an embodiment of the apparatus of the present invention showing one chamber placed in another chamber.

FIG. 3 shows a top view of the two chambers in another embodiment of the present invention. The apparatus comprises similar elements as that shown in FIG. 2, but they are configured differently. Chamber 4 is now located inside chamber 2. Chambers 2 and 4 are still separately connected to vacuum pump 16, enclosure 10, and pump 18 as shown in FIG. 3. Pump 18 usually is not needed when there is no steriliant flow between the two chambers. The two chambers are still independently operable. One of the advantages of the arrangement is that devices with greater length such as device 44 can be accommodated in the space between chamber 2 and chamber 4.

Chambers 2 and 4 share the top surface and the bottom surface, and are equipped with two sealable doors. Chamber 2 has a large door on the top surface and chamber 4 has a smaller door on the upper surface. The smaller door is in the large door, but the two doors can be operated independently.

Figure 4:
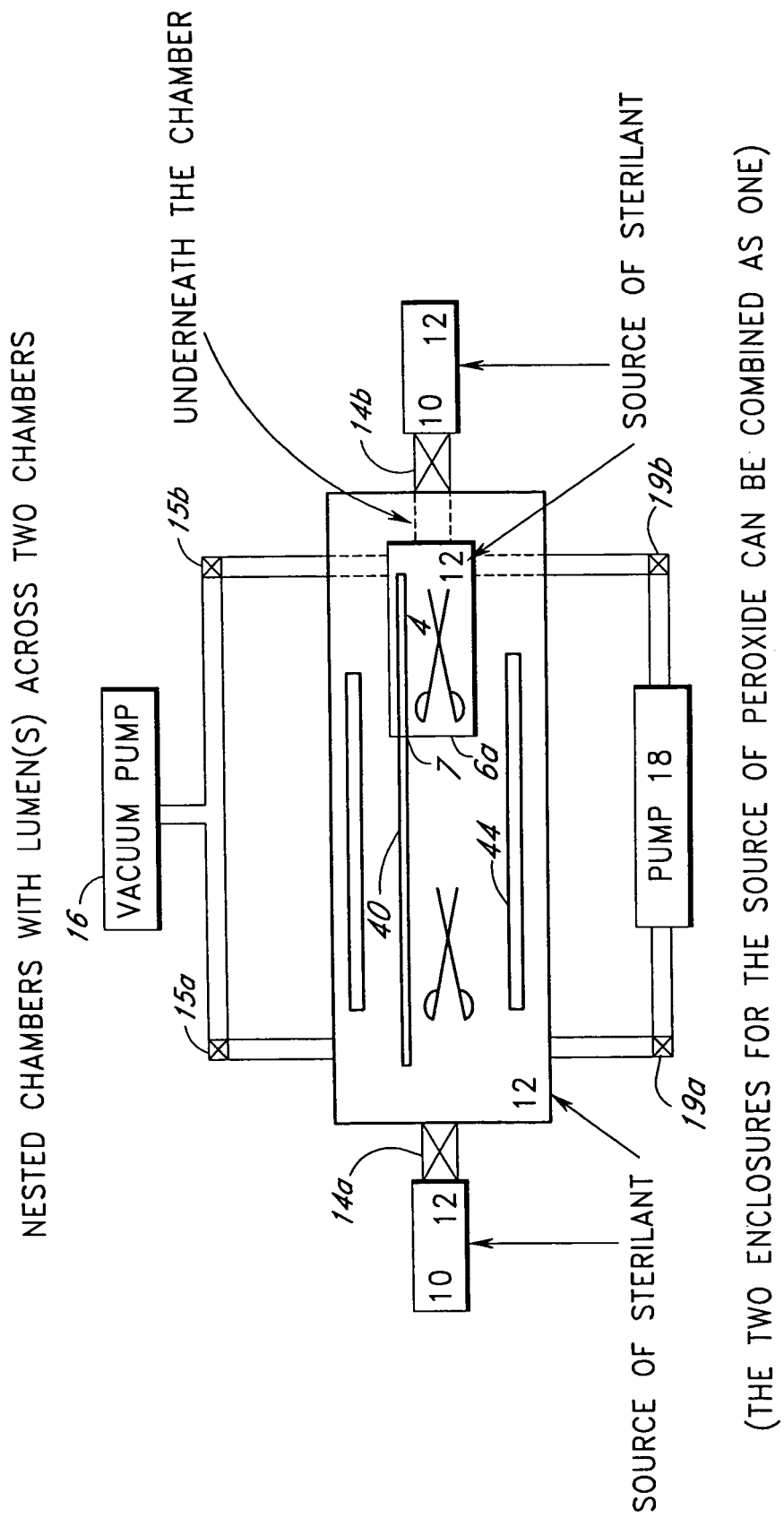
FIG. 4 is a schematic diagram of an embodiment of the apparatus of the present invention showing one chamber in another with lumen connecting the two chambers.

FIG. 4 shows an apparatus of the present invention similar to that shown in FIG. 3. The difference between the two embodiments shown in FIG. 3 and FIG. 4 is that in the apparatus of FIG. 4 chamber 2 and chamber 4 are in fluid communication through a lumen device 40. Therefore, this apparatus has all the advantages possessed by the apparatus of FIG. 3. In addition, it can be used to effectively sterilize devices with long narrow lumens. In this case, a removable interface 6a with an opening 7 is provided to accommodate the lumen device 40. The interface 6a can be installed in a similar way as discussed and shown in FIG. 1B. Valves 19a and 19b can be provided between pump 18 and the chambers.

FIG. 5 demonstrates the use of a container 20 in the chambers 2 and 4. For certain devices the sterility needs to be maintained after the sterilization. A sterilant vapor-permeable and microorganism-impermeable container is usually used to achieve the goal to keep the microorganism away form the sterilized devices after the devices have been sterilized. As shown in FIG. 5, a container 20 is placed in either chamber 2 or chamber 4, or both. The rest of the system is the same as the apparatus shown in FIG. 1A. The container is provided with a membrane (not shown) which is sterilant vapor-permeable and microorganism-impermeable and can be located at any convenient position on the wall of the container 20. The sterilant vapor-permeable and microorganism-impermeable membrane can be made of any conventional material known the art such as TYVEK™ nonwoven polyethylene fabric, nonwoven polypropylene such as SPUNGUARD™, or similar material. During a sterilization process, the sterilant vapor generated from a liquid sterilant in chamber 2 or 4 penetrates into the container 20 through the membrane and sterilizes the device placed inside the container 20. The devices to be sterilized can also be pretreated with liquid sterilant and then the liquid sterilant contained or absorbed by the devices is vaporized under vacuum applied through vacuum pump 16. Another option is to provide the container 20 with liquid sterilant before the sterilization process starts, then close a sealable door of the container 20, and apply vacuum to the container 20 to vaporized the liquid sterilant contained in the container 20. When the sterilization cycle is complete, the container is removed from the chamber. Because of the microorganism-impermeable feature, the container 20 can maintain the sterility of the device inside the container 20. This greatly reduces the chance of re-contamination during the handling of the sterilized device.

FIG. 6A shows a sterilization apparatus similar to that of FIG. 5. In the apparatus shown in FIG. 6A, a container 22 for lumen device 40 is placed across opening 7b in the interface 6c. The opening 7b is sealed around the outside of the container 22, for example, by an O-ring or other similar material mounted in the opening 7b. Container 22 also has an interface 22a with an opening 22b as shown in FIG. 6B. The opening 22b is also sealed around the outer surface of the, lumen device 40 so that no gas or vapor can flow therebetween when the seal is in gas-tight seal state. When desirable, the sealing between the outer surface of the lumen device 40 and the opening 22b of the interface 22a of the container 22 can be released so that the outer surface of the lumen device 40 adjacent the sealing is sterilized. A sterilant vapor-permeable and gas-permeable, but microorganism-impermeable membrane 24 is provided to both portions of the container 22 in chamber 2 and 4. The membrane 24 can be located at any convenient position on container 22, such as at both ends of the container 22. Through membranes 24 and lumen 42 of the lumen device 40, chamber 2 and chamber 4 are placed in fluid communication. By applying vacuum to either chamber with vacuum pump 16, a pressure differential can be established and a flow of sterilant is generated between the two chambers. The container 22 serves to maintain the sterility of the lumen device 40 placed therein following the sterilization.

Figure 7:
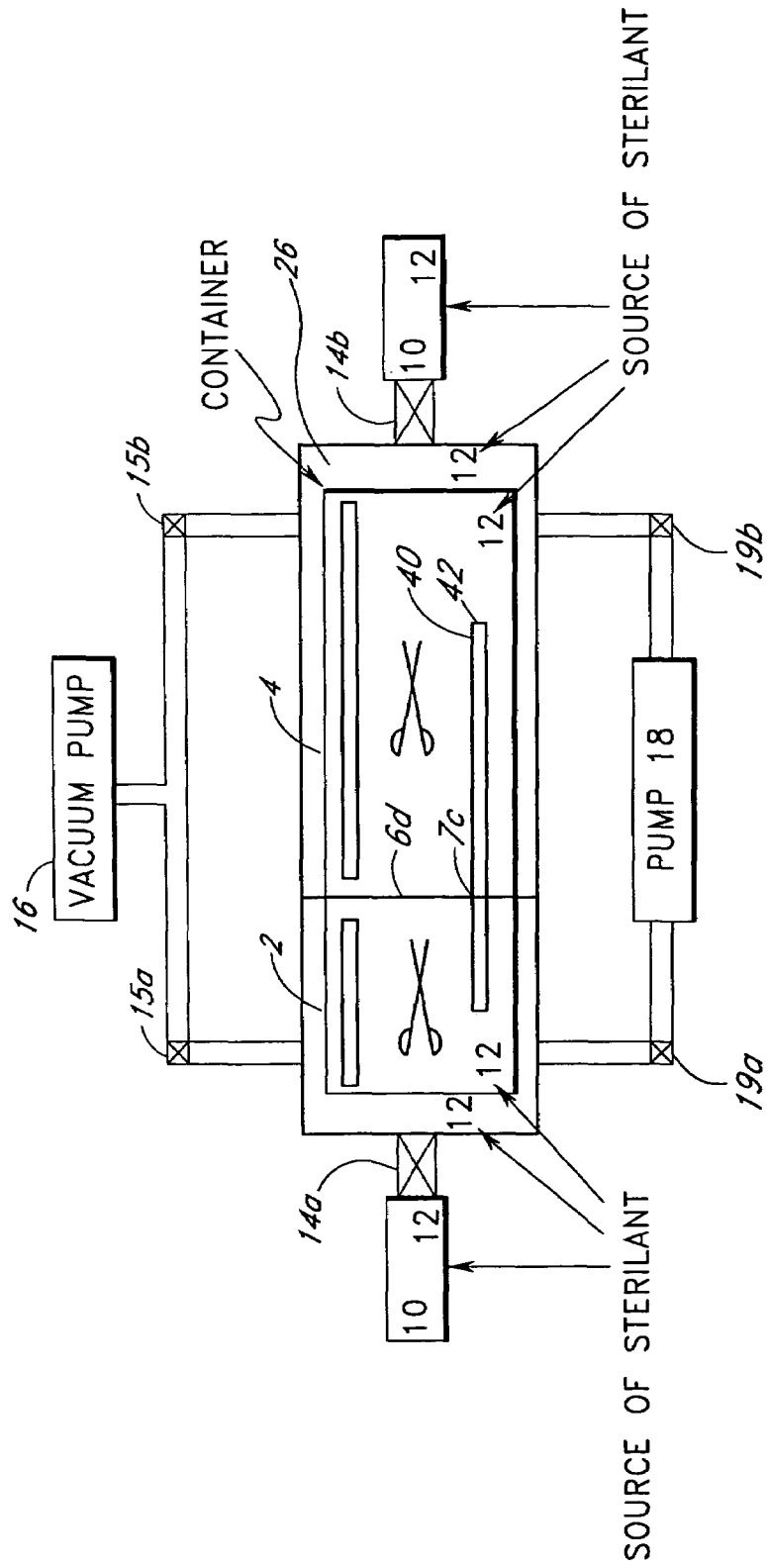
FIG. 7 is a schematic diagram of an embodiment of the apparatus of the present invention showing a container in the chambers separated with an interface.

FIG. 7 shows a sterilization apparatus which comprises a container 26. The container 26 is divided by an interface 6d. Like interface 6a described FIG. 2, interface 6d is sealable and has an opening 7c. Container 26 is accessible to sterilant source 12 or enclosure 10. The gap between the inner surface of chambers 2 and 4 and the outer surface of the container 26 is gas-tight sealed so that no air or sterilant vapor can flow through the gap from chamber 2 to chamber 4 or vice versa. In the embodiment shown in FIG. 7, the sealing of the gap between the inner surface of chambers 2 and 4 and the outer surface of the container 26 is provided at the about same location where the interface 6d separates the container 26 into two portions. The two portions of the container 26 separated by the interface 6d are in fluid communication through the lumen 42. The opening 7c is sealed around the outer surface of the lumen device 40 in the same manner as described in the section for the apparatus shown in FIG. 2. A sterilant vapor-permeable and gas-permeable, but microorganism-impermeable membrane is provided at both portions of the container 26. Thus, a pressure differential can be generated between the two chambers and between the two portions of the container 26 by means of vacuum pump 16 and/or pump 18. The pressure difference between the two portions of the container 26 forces sterilant fluid to flow through the lumen 42, and both the interior and the exterior of the lumen device 40 and other devices in the container 26 are efficiently sterilized. The sterility of the devices in the container 26 is maintained following the sterilization.

Figure 8:
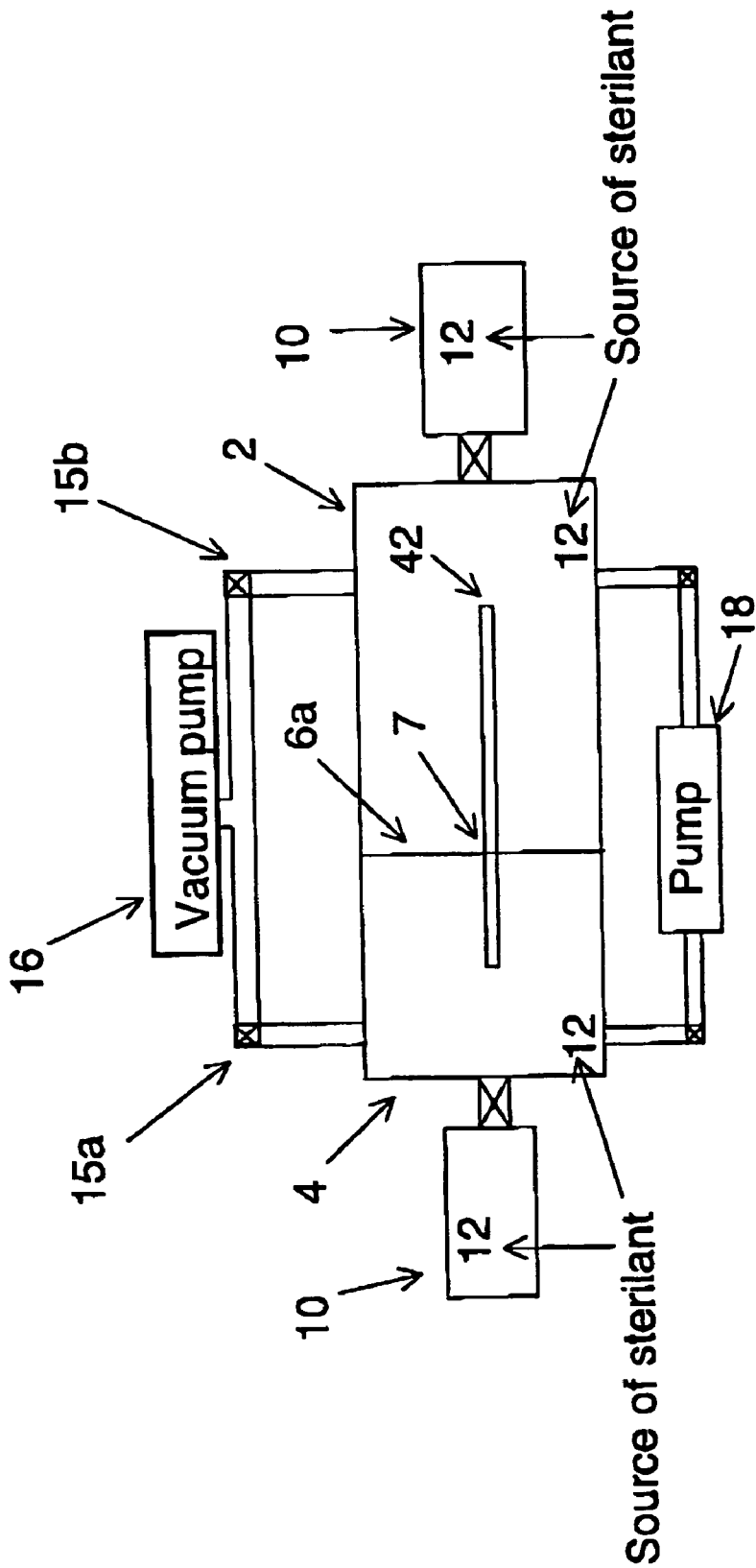
FIG. 8 is a schematic diagram of an alternative embodiment of the apparatus of FIG. 2, showing two compartments separated by an interface and in fluid communication through a lumen device.

FIG. 8 shows an apparatus similar to the apparatus shown in FIG. 2, except that only lumen device 40 is present in chambers 2 and 4. Lumen device 40 is placed into opening 7 in interface 6a between first chamber 2 and second chamber 4 so that part of lumen device 40 is in chamber 2, and part of lumen device 40 is in chamber 4. In the embodiment of FIG. 8, chamber 4 can be evacuated directly by the vacuum pump 16, through chamber 2, or both directly and through chamber 2. Sterilant can be circulated between chamber 2 and chamber 4 by pump 18.

In the apparatus of FIG. 8, a source of sterilant 12 can be located in chamber 4, chamber 2, either or both of the enclosures 10, both chamber 4 and chamber 2, or any combination thereof. The sterilant can be a liquid, vapor, or gas. In order to sterilize the interior of lumen 42, a pressure differential is created between the two ends of the lumen 42. The pressure gradient can be generated by pressurizing one end of lumen 42, for example, by introducing sterilant into either chamber 2 or chamber 4. If sterilant is introduced into chamber 4, the pressure in chamber 4 is higher than the pressure in chamber 2, and the sterilant flows from chamber 4 through lumen device 40 into chamber 2. If sterilant is introduced into chamber 2, the pressure in chamber 2 is higher than the pressure in chamber 4, and the sterilant flows from chamber 2 through the lumen device 40 into chamber 4. When sterilant is introduced into chamber 2 or chamber 4, the pressure in both chamber 2 and chamber 4 increases due to the introduction of sterilant and flowthrough of sterilant through lumen 42. In another embodiment, one end of the lumen 42 can be pressurized by circulating sterilant between chamber 2 and chamber 4 with pump 18.

Sterilant can be introduced into both chamber 2 and chamber 4 as long as there is a pressure difference between chamber 2 and chamber 4. In an embodiment, a pressure difference between chamber 2 and chamber 4 can be created by introducing sterilant into chamber 2 at a different rate than the rate at which sterilant is introduced into chamber 4. In another embodiment, a pressure difference between chamber 2 and chamber 4 is created with pump 18.

In an alternative embodiment, a pressure differential can be created between the two ends of lumen 42 by applying vacuum to one end of the lumen 42 with vacuum pump 16. In another embodiment, both vacuum pump 16 and pump 18 can be operated simultaneously or sequentially to create a pressure difference between the two ends of lumen 42. In yet another embodiment, both chambers 2 and 4 can be simultaneously be evacuated with vacuum pump 16, as long as there is a pressure difference between chamber 2 and chamber 4. The sterilant which flows between chamber 2 and chamber 4 through lumen 42 sterilizes the interior of the lumen 42. The sterilant inside chamber 2 and chamber 4 sterilizes the exterior of lumen device 40.

If the opening 7 includes a material which is permeable to the germicide, or if the opening 7 fits loosely around the outside of the lumen device 40, the germicide can flow around the outside of the lumen device 42 in the opening or can penetrate the material which is permeable to the germicide, thereby contacting and sterilizing the contact area between the outside of the lumen device and the opening 7 in the interface 6a.

The apparatus of FIG. 8 therefore provides an apparatus and a method for sterilizing the interior and the exterior of the lumen device 40. Placing the lumen device 40 into the opening 7 in the interface 6a provides a way to generate a pressure differential between the two ends of the lumen 42 of the lumen device 40 so that sterilant can flow through the interior of the lumen 40.

Figure 9:
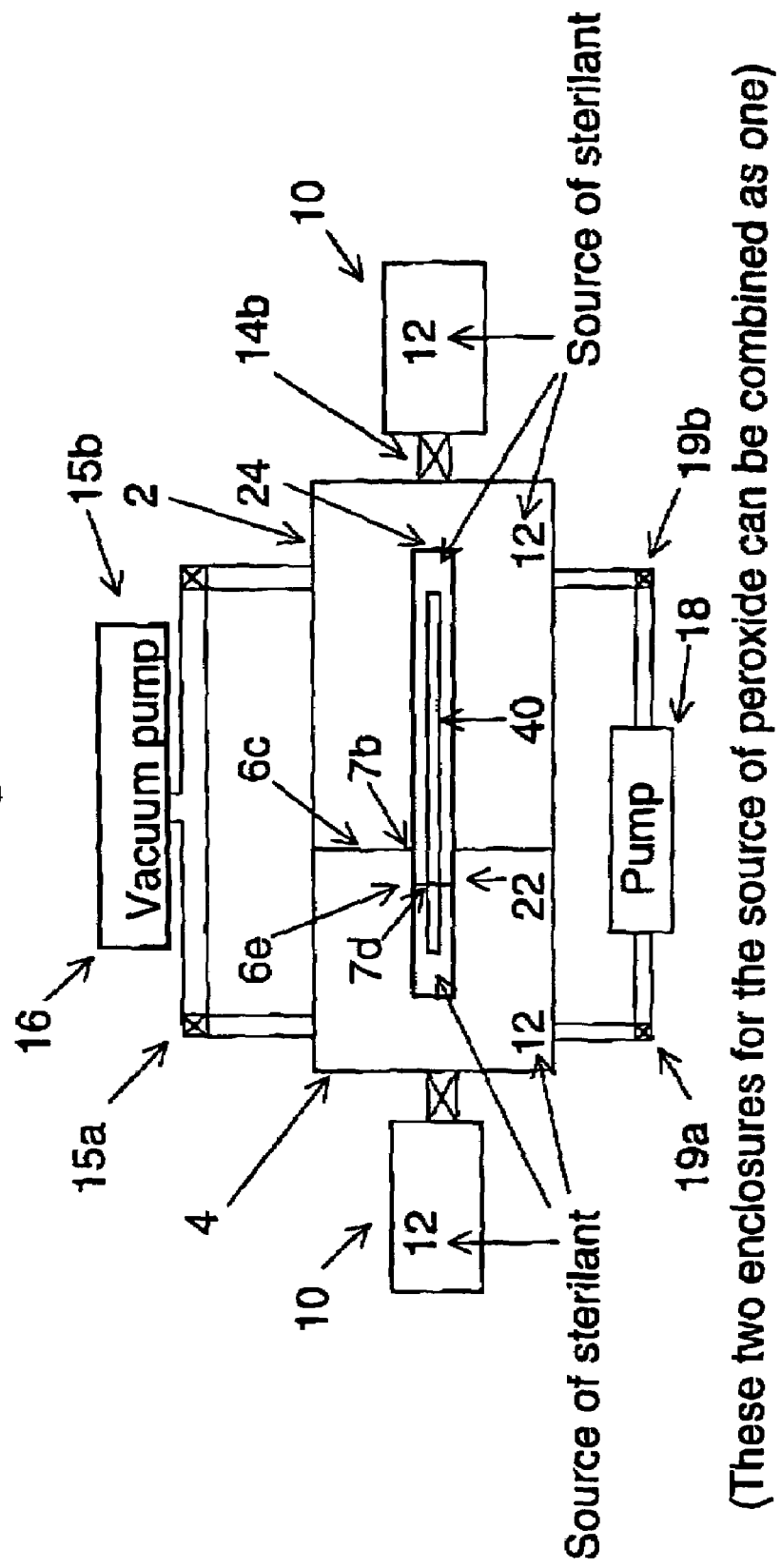
FIG. 9 is a schematic diagram of an alternative embodiment of the apparatus of FIG. 6A, showing a lumen in a container, where the container is placed into an interface between two chambers.
Figure 10:
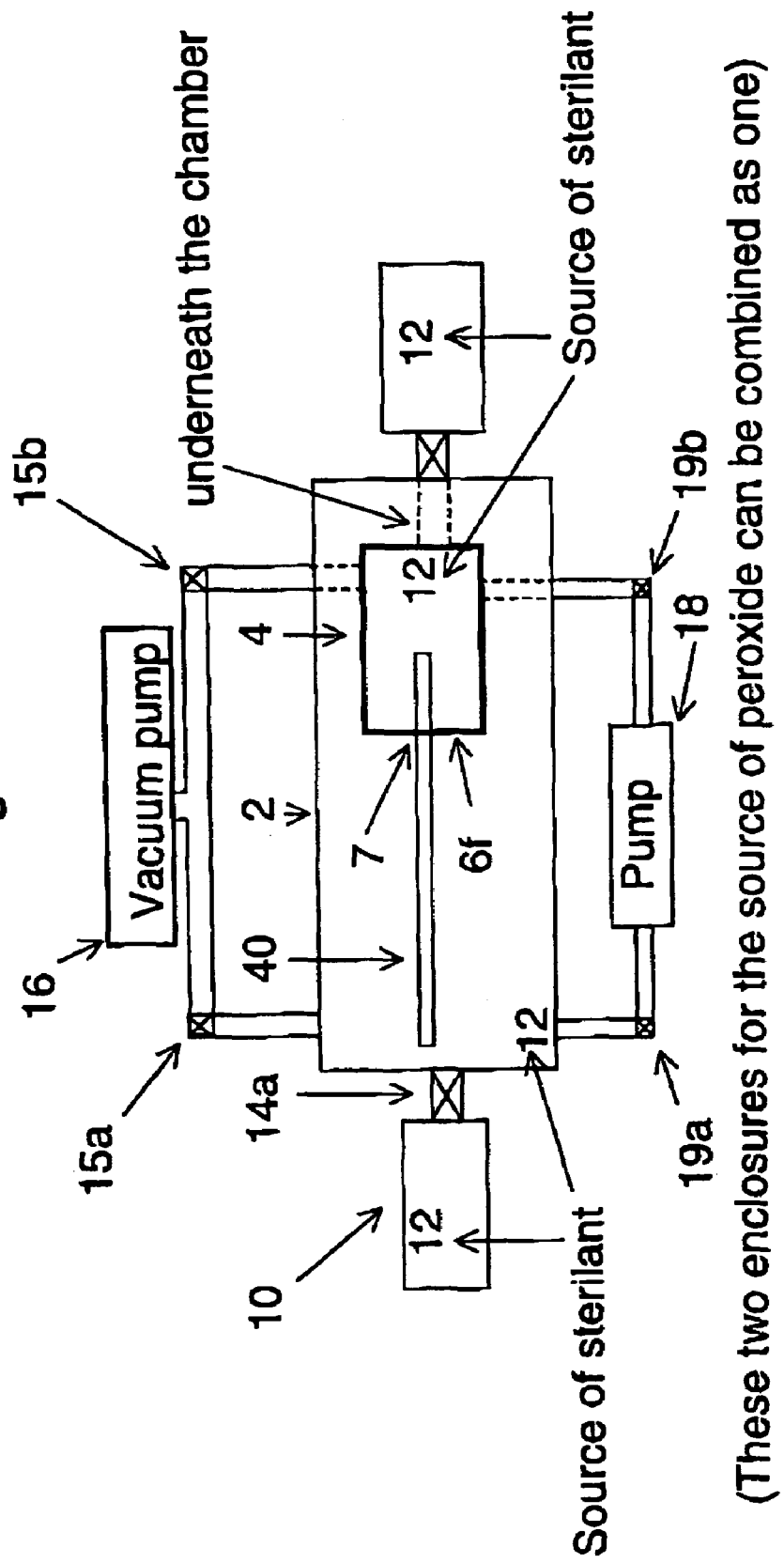
FIG. 10 is a schematic diagram of an alternative embodiment of the apparatus of FIG. 4, showing one chamber in another with a lumen connecting the two chambers.

FIG. 9 shows an apparatus similar to the apparatus of FIG. 6A. The apparatus of FIG. 9 differs from the apparatus of FIG. 6A in that only container 22 containing lumen device 40 is present in chambers 2 and 4. Container 22 is placed across opening 7b in the interface 6c. Lumen device 40 is then placed across opening 7d in interface 6e inside container 22. Container 22 is provided with at least one sterilant vapor-permeable and gas-permeable, but microorganism-impermeable membrane 24. In FIG. 10, two membranes 24 are present on the ends of the container 22. In other embodiments, the membranes 24 may be placed in other locations of the container 22.

A source of sterilant 12 is located in one or both of containers 10, chamber 2, and/or chamber 4 or any combination thereof. Creating a pressure difference between chamber 2 and chamber 4 leads to flow of sterilant through membrane 24 into container 22, through lumen device 40 and through the second membrane 24 into the other chamber. The flow of sterilant through the lumen device 40 sterilizes the lumen device 40. The container 22 protects the sterility of the lumen device 40, because the microorganism-impermeable membranes 24 prevent microorganisms from entering the interior of the container 22. The sterility of lumen device 40 inside container 22 is preserved even if container 22 is removed from chambers 2 and 4.

In an alternative embodiment, there is only one membrane 24 in the container 22. The container 22 is evacuated and sterilant is flowed through the container 22 and through membrane 24 to sterilize the lumen device 40.

FIG. 10 shows another apparatus similar to the apparatus shown in FIG. 4, except that only lumen device 40 is in chambers 2 and 4. Lumen device is placed through opening 7 in interface 6f of chamber 4. The area around the opening 7 may be made of a material which is permeable to the germicide. The germicide can penetrate the material and sterilize or disinfect the contact area between the interface and the lumen device.

A source of sterilant 12 is present in one or both of chambers 10, one or both of chambers 2 and 4, or any combination thereof. A pressure differential is created between chamber 2 and 4, thereby flowing sterilant between chamber 2 and chamber 4 through the interior of lumen device 40, thereby sterilizing the interior of the lumen device 40. The pressure difference can be caused by generating sterilant vapor, evacuating chamber 2 or chamber 4, pumping sterilant between chambers 2 and 4 with pump 16, or any combination thereof.

In an exemplary embodiment, chamber 2 is evacuated with the vacuum pump 16. Evacuating chamber 2 also evacuates chamber 4 and lumen device 40. An antimicrobial fluid is injected into chamber 2 or is generated from a source of antimicrobial fluid. The source of antimicrobial fluid can be in an enclosure 10 in fluid communication with chamber 2 or in chamber 2. Injection of the antimicrobial fluid into chamber 2 creates a higher pressure in chamber 2 than in chamber 4. The antimicrobial fluid flows from chamber 2 into chamber 4 through the lumen device 40 because of the pressure difference between chamber 2 and chamber 4, sterilizing interior of the lumen device 40. The antimicrobial fluid in chamber 2 sterilizes the exterior of the lumen device 40.

Chamber 2 may be evacuated again after sterilant flows through lumen device 40. Evacuating chamber 2 creates a pressure difference between chamber 2 and chamber 4, and the antimicrobial fluid flows from chamber 4 into chamber 2 because of the pressure difference. The flow of antimicrobial fluid from chamber 4 into chamber 2 through the lumen device 40 after evacuating chamber 2 again enhances the sterilization of the lumen device 40.

Alternatively, or in addition, chamber 2 may be vented. Venting chamber 2 creates a higher pressure in chamber 2 than in chamber 4, thereby driving antimicrobial fluid from chamber 2 into chamber 4 though lumen device 40. Venting chamber 2 therefore enhances the sterilization of the interior of the lumen device 40.

Center chamber 4 can also be evacuated by vacuum pump 16 through the line connected to valve 15b. Sterilant may be introduced into chamber 4 from a source of sterilant 12 inside chamber 4 or from a source of sterilant 12 in container 10. Vacuum pump 16 can evacuate both chamber 2 and chamber 4 simultaneously.

Opening 7 may contain a material which is permeable to the sterilant, thereby allowing the sterilant to penetrate the contact area between the exterior of the lumen device 40 and the interior of the opening 7, thereby sterilizing the contact area between the lumen device 40 and the opening 7.

Figure 11:
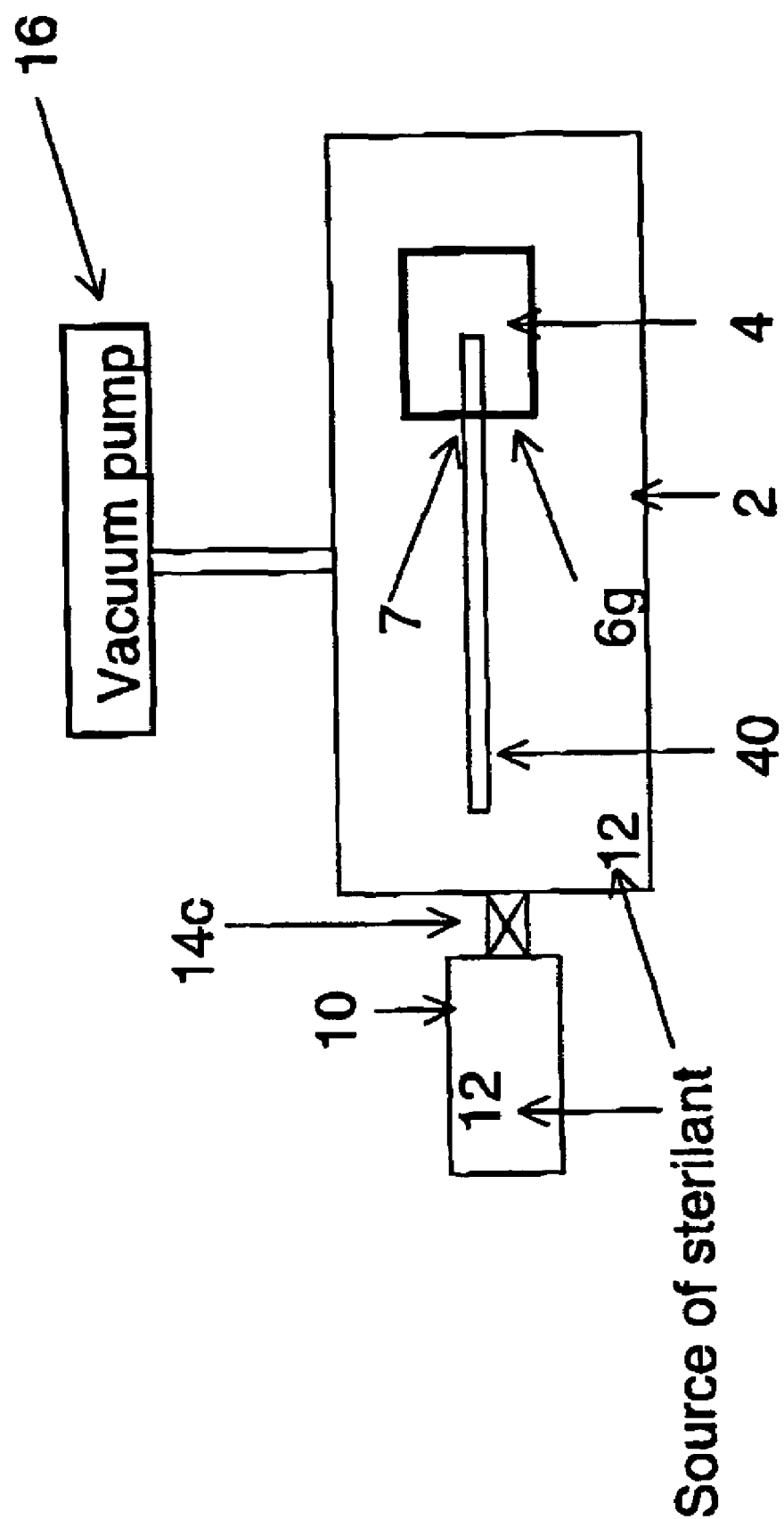
FIG. 11 is a schematic diagram of an alternative embodiment of the apparatus of FIG. 4, showing one chamber in another with a lumen connecting the two chambers.

FIG. 11 shows a simplified embodiment of the apparatus of FIG. 10. Lumen device 40 is placed though opening 7 in interface 6g on chamber 4. Chamber 4 is located inside chamber 2. Chamber 4 and chamber 2 are in fluid communication with vacuum pump 16. A source of sterilant 12 is present in container 10 and/or chamber 2. In an exemplary embodiment, the volume of chamber 4 is larger than the internal volume of lumen device 40.

Although the apparatus of FIG. 11 can be used in a variety of manners, in an exemplary embodiment, chambers 2 and 4 are evacuated with vacuum pump 16. A source of sterilant 12 is present in container 10. Sterilant is introduced into chamber 2 by opening valve 14c. The sterilant is drawn into chamber 4 through the lumen device 40 sterilizing the interior of lumen device 40. The exterior of the lumen device 40 is sterilized with the sterilant in chamber 2 and chamber 4.

Although a variety of sterilants can be used, a source of sterilant comprising peroxide is an exemplary sterilant. Aqueous hydrogen peroxide is a preferred source of sterilant. A solid source of peroxide is an alternative preferred source of sterilant. In an exemplary embodiment, plasma can be generated and contacted with the device to be sterilized or disinfected. The source of plasma can be inside chamber 2 or chamber 4, or the source of plasma can be outside chamber 2 and chamber 4, and plasma can be flowed into chamber 2, chamber 4, or both chamber 2 and chamber 4.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. A system for sterilizing a lumen device comprising:
   a chamber having at least one chamber interface in the chamber, wherein said at least one chamber interface in said chamber separates said chamber into a first area and a second area;
   a source of germicide; and
   a container inside said chamber, wherein at least a portion of said container is located in said first area of said chamber and at least a portion of said container is located in said second area of said chamber, said container comprising:
   at least one container interface in said container, wherein said at least one container interface in said container separates said container into at least a first compartment and a second compartment;
   at least one communication port in said container, wherein said at least one communication port provides fluid communication between said container and said chamber; and
   at least one lumen device extending across said at least one container interface in said container, whereby said first compartment is in fluid communication with said second compartment through said lumen device.

2. The system of claim 1, wherein said at least one container interface comprises at least one opening.

3. The system of claim 2, wherein said at least one opening is adjustable.

4. The system of claim 2, wherein said at least one container opening comprises a material which is permeable to germicide generated from said source of germicide, wherein said material is located at least in a contact area between said at least one container interface and said lumen device.

5. The system of claim 1, further comprising at least one vacuum pump to evacuate said chamber and/or said container.

6. The system of claim 1, wherein said source of germicide comprises hydrogen peroxide.

7. The system of claim 1, wherein said at least one communication port comprises a gas or vapor permeable membrane.

8. The system of claim 7, wherein said gas or vapor permeable membrane is impermeable to microorganisms.

9. The system of claim 1, wherein at least one communication port provides fluid communication between said first compartment and said chamber and at least one communication port provides fluid communication between said second compartment and said chamber.

* * * * *